(12) United States Patent
Rapp et al.

(10) Patent No.: US 7,572,769 B2
(45) Date of Patent: Aug. 11, 2009

(54) FIBRIN ADHESIVE GRANULATE AND METHOD FOR ITS PREPARATION

(75) Inventors: Mirna Rapp, Marburg (DE); Armin Prasch, Freiburg (DE); Bernhard Luy, Sulzburg (DE)

(73) Assignees: CSL Behring GmbH, Marburg (DE); Glatt Process Technology GmbH, Binzen (DE)

( * ) Notice: Subject to any disclaimer, the term of this patent is extended or adjusted under 35 U.S.C. 154(b) by 208 days.

(21) Appl. No.: 11/826,072

(22) Filed: Jul. 12, 2007

(65) Prior Publication Data

US 2008/0003272 A1 Jan. 3, 2008

Related U.S. Application Data

(63) Continuation of application No. 09/869,031, filed as application No. PCT/EP99/06898 on Sep. 17, 1999, now abandoned.

(30) Foreign Application Priority Data

| Dec. 23, 1998 | (DE) | ................. | 198 59 611 |
| Jun. 21, 1999 | (DE) | ................. | 199 28 371 |
| Jun. 21, 1999 | (DE) | ................. | 199 28 372 |

(51) Int. Cl.
*C07K 14/00* (2006.01)
(52) U.S. Cl. ......................................... 514/2
(58) Field of Classification Search .................. None
See application file for complete search history.

(56) References Cited

U.S. PATENT DOCUMENTS

| 4,427,651 | A | 1/1984 | Stroetmann |
| 4,453,939 | A | 6/1984 | Zimmerman et al. |
| 6,596,318 | B2 | 7/2003 | Prasch et al. |
| 2002/0037323 | A1 | 3/2002 | Prasch et al. |
| 2003/0143518 | A1 | 7/2003 | Luck et al. |

FOREIGN PATENT DOCUMENTS

| DE | 44 41 167 C1 | 3/1996 |
| DE | A-100 12 732 | 9/2001 |
| EP | 0 792 188 | 9/1994 |
| WO | WO 92/22312 | 12/1992 |
| WO | WO 96/22115 | 7/1996 |
| WO | WO 96/29990 | 10/1996 |
| WO | WO 97/28832 | 8/1997 |
| WO | WO 97/44015 | 11/1997 |
| WO | WO 99/15637 | 4/1999 |

OTHER PUBLICATIONS

Abstract of EP 0 792 188 dated Sep. 3, 1997, from Esp@cenet Database.
English-language translation of DE 44 41 167 C1 (Mar. 14, 1990).
English-language translation of German Patent Application No. DE-A-10012732 (Sep. 20, 2001).
Decision dated Dec. 18, 2002, from the German Patent Office in case No. 198 49 589.7-45.
Chabbat, J., et al., "Properties of a new fibrin glue stable in liquid state," Thrombosis Research, 76(6):525-533 (1994).
De Iaco, PierAndrea, et al., "Fibrin sealant in laparoscopic adhesion prevention in the rabbit uterine horn model," Fertility and Sterility, 62(2):400-404 (1994).
Evrard, V.A.C., et al., "Peritoneal healing after fibrin glue application: a comparative study in a rat model," Human Reproduction, 11(9):1877-1880 (1996).
Gauwerky, J.F.H., et al., "The effect of fibrin glue and peritoneal grafts in the prevention of intraperitonael adhesions," Arch. Gynecol. Obstet., 247:161-166 (1990).
Lindenberg, S., et al., "Prevention of peritoneal adhesion formation by fibrin sealant," Annales Chirurgiae et Gynaecologiae, 73:11-13 (1984).
Moro, Hisanaga, et al., "The effect of fibrin glue on inhibition of pericardial adhesions," The Japanese Journal of Thoracic and Cardiovascular Surgery, 47(2):79-84 (1999).
Takeuchi, Hiroyuki, et al., "Effects of fibrin glue on postsurgical adhesions after uterine or ovarian surgery in rabbits," J. Obstet. Gynaecol. Res., 23(5):479-484 (1997).
Voight, Rudolf, et al., "Lehrbuch der pharmazeutischen technologie," 85 0570 EPO; Verla chemie (1984).
English-language translation of Voight, Rudolf, et al., "Lehrbuch der pharmazeutischen technologie," 85 0570 EPO; Verla chemie (1984).
Prunkard, D., et al., "Heterologous production of recominant human fibrinogen, thrombin, and factor XIII as components of completely recombinant fibrin sealants," Thrombosis and Haemostasis 9:372 (1997).
Schuefer, Torben, et al., "Control of fluidized bed granulation v. factors affecting granule growth," Arch. Pharm. Chemi, Sci. Ed., 6:68-82 (1978).
International Search Report for PCT/EP99/06898 (WO 00/38752) dated Dec. 21, 1999.
International Search Report for PCT/EP00/08128 (WO 00/024436) dated Jan. 25, 2000.

*Primary Examiner*—Karen Cochrane Carlson
(74) *Attorney, Agent, or Firm*—Finnegan, Henderson, Farabow, Garrett & Dunner, L.L.P.

(57) ABSTRACT

The invention relates to a flowable fibrin adhesive granulate containing thrombin, Factor XIII, fibrinogen, and a calcium salt in the form of granules with a particle size of more than 50 μm to 1000 μm. Said granulate is useful for the healing of wounds in surgery, tissue therapy and/or as supporting material for biological factors. The invention also relates to an effervescent granulate and an effervescent powder for producing a foam that is suitable for hemostasis. The invention further relates to preparations to arrest bleeding containing a non-woven fabric for wounds consisting of a biodegradable supporting material that is coated with a fibrin glue granulate mixture or mixed granulate.

24 Claims, No Drawings

FIBRIN ADHESIVE GRANULATE AND METHOD FOR ITS PREPARATION

This is a continuation of U.S. Application Ser. No. 09/869,031, which has a § 371 filing date of Oct. 16, 2001, now abandoned, and which is the U.S. National Stage Application of International Application No. PCT/EP99/06898 (WO 00/38752), filed on Sept. 17, 1999, which claims priority from: German Application No. DE 198 59 611.1, filed on Dec. 23, 1998; German Application No. DE 199 28 372.9, filed on Jun. 21, 1999; and German Application No. DE 199 28 371.0, filed on Jun. 21, 1999. All applications cited above are incorporated by reference herein.

The object of the invention is a flowable fibrin adhesive granulate that contains all substances required for the formation of a stable fibrin gel and can be used directly for wound adhesion. It is generated by spray drying in a fluidized bed by means of a fluidization gas.

It is known that after the creation of a wound, wound healing is initiated through an activation cascade of several subsequent coagulation factors. This finally leads to the reaction between the activated thrombin and fibrinogen in the presence of calcium ions to form a fibrin matrix that covers the wound and thus leads to hemostasis. Said fibrin matrix is further strengthened by the activated Factor XIII (F XIIIa) through additional covalent bonds, which increases the mechanical stability of said fibrin matrix and makes it resistant to premature proteolytical degradation.

In modern surgery, hemostasis continues to gain in significance because of fibrin adhesion and because so-called fibrin adhesives are a well tolerated biomaterial that promotes wound healing. The method is excellently suited for the hemostasis of strongly bleeding wounds during surgery on parenchymatous inner organs, skin transplants, in emergency surgery for internal and external injuries, but primarily also as a supporting seal for sutures to avoid postoperative bleeding. In ear, nose and throat surgery and facial surgery, fibrin adhesive is preferred to sutures for cosmetic reasons for the healing of external wounds. Fibrin adhesive is also used increasingly in endoscopic surgery, for example to arrest bleeding in stomach ulcers.

In addition to inorganic salts and amino acids, the currently available commercial fibrin adhesives such as Beriplast® also contain the coagulation factors fibrinogen, thrombin and Factor XIII, which are obtained from human plasma, as well as albumin and fibronectin to promote wound healing. Although the preparation exhibits good biochemical and haemostatic properties, it requires extensive preparations prior to use. The separate fibrinogen- and thrombin lyophilisates are dissolved separately, drawn into two separate syringes, and clamped into a special holding device. This process is time-consuming and requires specially trained personnel. A variant of the fibrin adhesive is already commercially available in dissolved form in the syringes under the name Tissucol®, but it can be stored only at low temperatures of −20° Celsius and requires defrosting in a water bath prior to use. Thus, both variants of the fibrin adhesive cannot be used in situations that call for a ready-to-use fibrin adhesive that does not require advance preparation. Furthermore, a ready-to-use and easily dosable fibrin adhesive would be more economical simply because it would avoid needless preparations or the discarding of excess material.

A possible improvement in the handling of the fibrin adhesive could be a one-component-adhesive that contains all components necessary for the formation of the fibrin in one compartment. However, the development of a one-component adhesive in an aqueous solution is extremely difficult to realize in practice. The only possibility may be to mix the components of the fibrin glue in dry condition so they would dissolve in the blood fluid or the wound exudate after being applied to the wound and then form a fibrin matrix in situ, which would lead to hemostasis. This would also require transforming the fibrinogen, which by nature does not dissolve easily, into a dry form from which it would dissolve quickly while at the same time immediately reacting with the thrombin.

There have also been attempts to use a specific lyophilisation process to develop particles containing fibrinogen and thrombin, which are mixed after preparation and activated in the wound. Thus, international patent application WO 97/44015 describes the preparation of so-called micro particles on which fibrinogen and thrombin are spray-dried individually. Over 90% of said particles have a grain size of up to 20 μm. They should dissolve well and can be mixed and used for wound healing. However, a disadvantage of said micro particles is that they form a very dusty powder, which makes a direct application to the wound impossible. Thus, a powder of this type requires a special application system, which drastically reduces its handling and clinical indications.

The problem was therefore to develop a fibrin adhesive granulate that dissolves well, is flowable, is not dusty, and can therefore be applied directly to the wound, for example, in the principle of a salt shaker.

The problem is solved in accordance with the invention by a flowable fibrin adhesive granulate containing thrombin, Factor XIII, fibrinogen and a calcium salt in pellets with a particle size of more than 50 to approximately 1000 μm, preferably with a particle size of 100 to 200 μm. Because of the particle size, the fibrin adhesive in accordance with the invention is not dusty, dissolves well, is flowable, and is excellently suited for application to a wound surface or moist tissue, where it immediately forms a fibrin matrix.

Albumin, fibronectin, amino acids and physiologically safe inorganic salts can be added to a fibrin adhesive granulate of this type. Furthermore, it can also be used as a release system for biological, vegetable and/or synthetic factors. These factors can support wound healing or act as antifibrinolytic, antibiotic, chemotherapeutic, or immune modulators. They are added to the fibrin adhesive granulate during the spray drying process.

An appropriate principal method for the preparation of the fibrin adhesive granulate in accordance with the invention is already known from the international patent application WO 96/15849, which describes a method for the drying of blood plasma, blood plasma fractions, or blood plasma products obtained therefrom, where the treatment product is sprayed in liquid or dissolved condition into an evacuatable container which performs the drying—up to granulate form—by means of a fluidization gas in a fluidized bed. However, this method cannot be readily applied to fibrinogen and thrombin because it is known that these substances react to fibrin after coming into contact with aqueous solutions. Therefore, the use of aqueous solutions is not an option for the spray drying of these components. To obtain both components in one particle nevertheless, the components in accordance with the invention are suspended together in one single organic solvent and spray dried from it. Fibrinogen, thrombin and Factor XIII can also be more or less homogeneously suspended in organic solvents such as the lower alcohols, preferably isopropanol or ethanol, acetone, nitrilene, liquid carboxylic acid esters, ethers, chloroform, dimethyl formamide and dimethyl sulfoxide, also in the presence of $CaCl_2$, without exhibiting a reaction to fibrin. After the organic solvent is removed, they are again capable of fibrin formation in the aqueous phase.

In accordance with the invention, spray drying is performed either with a top-spray-process, where the liquid is supplied to the fluidization gas in the counter current, or in co-current flow (bottom-spray-process). A fine distribution is achieved by spraying the liquid treatment product into the evacuatable container through an appropriate nozzle. In this way, the fluidization gas swirls the product to be treated and also transfers heat. For this reason, a heated gas is used as fluidization gas. Gentle drying can be maintained by measuring the product temperature during the fluidization bed process controlling the process on the basis of said measurements. Either air or an inert gas such as nitrogen can be used as a fluidization gas. The drying is continued until the treatment product is available in finely dispersed granulate form with a particle size of 50 to approximately 1000 µm, preferably 100 to 200 µm.

The fibrin granulate adhesive in accordance with the invention can be produced in the evacuatable container with or without a support medium as a receiver. Appropriate support media are primarily sugar and sugar alcohols such as saccharose, lactose or mannitol, which have a good bio-tolerance. However, it is also possible to use proteins such as serum albumin as a support medium. It is especially preferred to use the fibrin adhesive component itself, i.e., fibrinogen, Factor XIII, thrombin, $CaCl_2$ or their mixtures, in powder condition as a support medium. The aqueous solution or suspension of the fibrin adhesive component in organic solvent is then sprayed onto said support medium to form a granulate. This makes obsolete the addition of a further support medium such as a sugar, mannitol or albumin.

An especially preferred method is two-phase spray drying where a fibrinogen granulate is prepared first. In addition to fibrinogen, said granulate can also contain other proteins, carbohydrates, amino acids and physiologically safe inorganic salts, and also calcium salt as well. The particle size of said granulate is more than 50 and up to approximately 1000 µm, with the preferred particle size being between 100 and 200 µm. A fine thrombin suspension in an organic solvent is sprayed onto said fibrinogen granulate. Said thrombin suspension can comprise dissolved calcium ions unless they were added already to the fibrinogen granulate. The concentration of the calcium ions is 1 to 100 mM, preferably 10 to 50 mM. This yields a fibrin adhesive granulate with a particle size that is preferably between 100 and 200 µm and has a grainy structure that dissolves very well. This does not yield any compact particles such as small pellets, but rather a granulate with many tiny channels. In this way, it is possible to obtain a relatively large particle size, which renders the product simultaneously free of dust and is very soluble, similar to the known instant coffee. This granulate is also excellently suited to be applied to a wound surface and immediately forms a solid and elastic fibrin gel after it comes into contact with an aqueous medium.

The fibrin adhesive granulate in accordance with the invention can also be obtained by spray-drying fibrinogen concentrate from an aqueous solution on a receiver, such as mannitol.

To that end, a fibrinogen/mannitol-granulate is obtained first, and then thrombin/calcium salt, for example from an isopropanolic suspension, is sprayed onto said granulate. The organic solvent prevents the formation of fibrin following the contact between fibrinogen and the thrombin.

Finally, it is also possible to prepare separate fibrinogen- and thrombin granulates with the aforementioned particle size in separate processes, whereby both substances can be spray-dried from aqueous solutions. However, for the preparation of the thrombin granulate, this would require a sufficient portion of a support medium because the quantity of thrombin in the fibrin adhesive is smaller by a factor of $10^2$ to $10^3$ than the quantity of fibrinogen. The two granulates are then mixed and can be used appropriately for hemostasis and wound healing.

The fibrinogen adhesive granulates prepared in accordance with the aforementioned method were then tested as to their biomechanical properties and the following results were obtained:

Tear strength following in vitro tissue gluing (adhesion surface: 2.25 $cm^2$)

Results of a comparative study based on a randomization list on the tear strength of the uniform granulate (thrombin, fibrinogen and Factor XIII in one particle), the granulate mixture (fibrinogen granulate+thrombin granulate) and the fluid fibrin adhesive (Beriplast®):

| Test substance | Tear Strength |
| --- | --- |
| Uniform granulate (mixed granulate) | 3.3 N |
| Granulate mixture | 1.8 N |
| Beriplast ® | 1.5 N |

The measured values clearly show the advantage of the uniform granulate (mixed granulate) compared to the granulate mixture with respect to the biomechanical properties. The quantity of active components was nearly identical in all three testing substances.

Additionally, the fibrin adhesive granulate in accordance with the invention can be stored at room temperature as well as at temperatures of 2-8° Celsius for at least 6 to 8 months without any noticeable loss of activity in the individual components.

The flowable fibrin adhesive granulate in accordance with the invention distinguishes itself from the previously known fibrin adhesives in that it is easier to handle, does not require any preparatory measures and is always in a ready-to-use condition. It is therefore particularly suitable for emergency surgery. It also has the advantage of an extraordinarily simple use in that it can be applied to wound surfaces in the same way as using a saltshaker. It is excellently suited for surgical applications where the objective is to achieve a quick hemostasis by soaking up blood with simultaneous fibrin adhesion.

Although the aforementioned granulates simplify the use of the fibrin adhesive significantly and reduce high-effort surgery preparations that require specially trained personnel and appropriate devices, there is a continued demand for simple fibrin adhesive preparations that should be in every physician's emergency bag and can be used immediately at the site of an accident without lengthy preparations.

It was possible to find a solution for this problem by developing an effervescent granulate or an effervescent powder to generate a foam that is suitable for hemostasis and contains the substances required for the formation of $CO_2$ in addition to the granulate mixture or mixed granulate according to the invention containing fibrinogen, Factor XIII, thrombin and a soluble calcium salt.

In addition to many other advantages, the effervescent granulate or effervescent powder in accordance with the invention also has the advantage of loosening up the granulate mass through the foaming, which allows the liquid easier access into the interior on the granulate pellets. This leads quite quickly to the creation of stable fibrin foam that covers the bleeding wound and quickly arrests the bleeding. The formation of the foam can take place directly on the wound, with the wound secretions providing the moisture needed to create the foam. It is also possible, though, to create the foam in a dish or on a plate by adding liquid, and then placing the finished foam on the bleeding wound. Because of its tremendous flexibility, the foam created in this way cannot only be used for the external covering of wounds, but also for bleeding wounds during surgery, where the foam is packed into the bleeding surgery wound and places itself on the bleeding tissue to quickly arrests the bleeding.

There is room for further improvement in the therapeutic value of the effervescent granulate or effervescent powder in accordance with the invention if biological, vegetable or synthetic active substances that promote wound healing, such as immunoglobulins, chemotherapeutics or antibiotics, are added to said effervescent granulate or powder. These substances are sprayed on the flowable, dry fibrin adhesive granulate during the production of the granulate or the effervescent powder or are mixed therewith. It is also possible to make an effervescent tablet from said mixture, which contains the ingredients for the preparation of a foam that is suitable for hemostasis in a form that is in a precise dosage and easy to handle.

It is generally sufficient to apply the effervescent granulate or effervescent powder in accordance with the invention in a quantity that contains, depending of the size of the bleeding wound, fibrinogen in a quantity of 0.1 to 2.5 grams and thrombin in a quantity of less than 10 I.E. If an effervescent tablet is used, said tablets can also have imprinted breaking grooves that allow breaking off part of a tablet to arrest bleeding in smaller wounds if the quantity of foam generated with part of the tablet is already sufficient to arrest the bleeding.

In addition, the granulate mixtures or mixed granulates in accordance with the invention can also be used to produce galenic preparations that are excellently suited for hemostasis, can be used in a very simple manner, and are available immediately at the site of an accident without requiring lengthy preparations.

This objective is achieved with a biodegradable wound fleece that is able to arrest bleeding even on larger wound surfaces. To that end, a fibrin adhesive granulate is applied, either directly or in combination with a biocompatible auxiliary, to a support medium that is comprised of a biodegradable polymer in which the fibrin adhesive is embedded. A suitable support medium for this purpose is primarily natural or chemically modified collagen, keratin, gelatin, carbohydrates or cellulose derivatives. The support medium can also be comprised of a synthetic, biodegradable polymer. Suitable polymers include polyhydroxy carboxylic acids, polyesters, polycyanoacrylate, polyaminoacids, polyalcohols as well as silicon. A preparation is applied to said support medium which preferably contains fibrinogen in a quantity of 0.05 to 50 mg/cm$^2$, preferably 1 to 20 mg/cm$^2$, as well as thrombin in a quantity of 1 μg to 10 mg/cm$^2$, preferably 0.05 to 2 mg/cm$^2$. To improve adhesion, polyethylene glycol (PEG) with a suitable molecule size or a mixture of several polyethylene glycols of various molecule sizes can be added to the fibrin adhesive preparation as auxiliaries.

A further improvement in hemostasis can be achieved by applying the aforementioned wound care fleece to a bandage or plaster bandage. Said bandage should be coated with a wound care fleece in accordance with the invention on the side that will be applied to the bleeding wound. Polyethylene glycol 4000 or polyethylene glycol 6000 or mixtures thereof are preferably used for the preparation of the bandages in accordance with the invention. To prepare the coating, the polyethylene glycol is dissolved in an organic solvent, preferably isopropanol, which is used in a concentration of 0.5 to 70%, preferably in a concentration of 5 to 30% (w/v). The fibrin adhesive granulate is spread on the bandage and then wetted with the isopropanol-polyethylene glycol 6000-solution. After the organic solvent has evaporated, the resulting biodegradable wound care fleece has a fibrin adhesive coating with good adhesion. The organic solvent is excellently suited for the coating because it evaporates easily, prevents a reaction with fibrin and ensures that the activity of the individual components is maintained. Furthermore, the granulate form is maintained after treatment in the organic solvent, preferably isopropanol.

The aforementioned, haemostatic, salve- or gel-type preparation is generally applied only to one side of the wound care fleece in accordance with the invention. However, there are application cases where it is preferable to coat both sides of the wound care fleece. If the wound is covered with this type of bandage, the haemostatic effect of the fibrin adhesive will unfold directly on the wound as soon as the fibrin is formed from the action of the wound secretion and the components in the bandage. In many cases, the application can be simplified further by applying the wound care fleece in accordance with the invention to a waterproof or water-permeable surface material suitable for plaster preparation, whereby room is left on the side for adhesive strips that are coated with a physiologically safe adhesive. This type of plaster can be used quickly and permanently to cover the bleeding wound in a simple way und leads to a quick hemostasis.

Hemostasis can also be achieved in a simple way by embedding the particles of a fibrin adhesive into a salve- or gel-type preparation comprised of a hydrophilic, non-aqueous salve base. Especially suitable for a hydrophilic, non-aqueous salve base are polyols, for example polyethylene glycols, polypropylene glycols or ethylene propylene copolymers in which the particles of the fibrin adhesive are evenly distributed and which take up the moisture contained in the wound secretions. Once moisture enters, the components of the fibrin adhesive immediately form a fibrin mesh that quickly and effectively covers the wound and arrests the bleeding. It is obvious that salve bases that contain fats or are water-repellent are not suitable for this use.

The fibrin adhesive contained in the preparations in accordance with the invention contains a dry mixture of fibrinogen, Factor XIII, thrombin and a soluble calcium salt. The preparation can be also appropriately filled into a salve tube and can then be stored over a long period of time and readily used in this form.

It goes without saying that the effectiveness of the aforementioned preparations to achieve hemostasis is guaranteed only if any addition of aqueous fluids and thus a premature formation of fibrin is avoided prior to their use. This must also be taken into account during the production of the preparations, when the granulate mixtures or the mixed granulates in accordance with the invention are impasted with the hydrophilic, but non-aqueous salve-base in the known manner. The salve- or gel-type preparation obtained in this way can then be applied to the biodegradable support medium to prepare a wound care fleece, or it can be used directly.

A further improvement of the preparations in accordance with the invention can be achieved if other biological, vegetable or synthetic active substances such as immunoglobulin, chemotherapeutics, or antibiotics are added in addition to the fibrin adhesive.

The wound care fleece in accordance with the invention, the bandage or plaster, or the salve- or gel-type preparation can be used in a simple and effective manner for the hemostasis of interior and exterior wounds.

The invention is explained by the following examples.

EXAMPLE 1

Preparation of Fibrinogen Granulate without Support Medium as Receiver

A 10% protein solution of Beriplast®-fibrinogen concentrate (also contains F XIII) was spray dried according to the top-spray-method in a fluidized bed. Said process was performed in a GPCG 1-facility by Glatt GmbH and is claimed and described in detail in International Patent Application WO 96/15849. The conditions were:

| | |
|---|---|
| Input temperature: | 37° Celsius |
| Output temperature: | 30° Celsius |
| Spraying pressure: | 3.0 bar |
| Spraying rate: | 3.2 g/min |

The fibrinogen granulate prepared in this way had a mean particle size of 100 μm and dissolved very well. Analytical measurements of the activity showed that the activity of fibrinogen and F XIII was not negatively affected by the spray drying process under the aforementioned conditions.

EXAMPLE 2

Preparation of Fibrinogen Granulates with Support Medium as Receiver 200 grams of mannitol or albumin was placed in the spray-drying chamber. 100 grams of fibrinogen concentrate was sprayed on the receiver in the fluidized bed under the following conditions:

| | |
|---|---|
| Input temperature: | 30° Celsius |
| Output temperature: | 24° Celsius |
| Spraying pressure: | 2.5 bar |
| Spraying rate: | 3.0 to 8.0 g/min |

The resulting granulate was flowable, dissolved very well, and had a mean particle size of 100 μm, with full recovery of the fibrinogen- and F XIII activity.

EXAMPLE 3

Preparation of Fibrin Adhesive Granulate

An isopropanolic thrombin/$CaCl_2$-suspension was sprayed on the fibrinogen granulate prepared in Examples 1 or 2. The process conditions were as follows:

| | |
|---|---|
| Input temperature: | 30° Celsius |
| Output temperature: | 25° Celsius |
| Spraying pressure: | 2.5 bar |
| Spraying rate: | 3.0 to 8.0 g/min |

The fibrin adhesive granulate prepared in this manner had a mean particle size of 100 μm; it was flowable, did not give off dust, immediately formed a stable fibrin coagulum after coming into contact with an aqueous solution, and was rendered covalent by F XIII.

EXAMPLE 4

Preparation of Thrombin Granulate

An aqueous 0.3% thrombin solution was sprayed on a mannitol or human serum albumin receiver. The conditions were as follows:

| | |
|---|---|
| Input temperature: | 30° Celsius |
| Output temperature: | 23° Celsius |
| Spraying pressure: | 2.5 bar |
| Spraying rate: | 4.2 g/min |

The resulting granulate had a mean particle size of approximately 65 μm; it was flowable and did not give off dust. It mixed well with the fibrinogen granulate and was also suitable for use as fibrin adhesive.

EXAMPLE 5

Preparation of a Fibrin Adhesive Granulate from an Isopropanolic Suspension Containing All Fibrin Adhesive Components An isopropanolic suspension containing all fibrin adhesive components, i.e., fibrinogen, Factor XIII, thrombin, $CaCl_2$ or mixtures thereof, was sprayed into a spray-drying chamber according to Examples 1 and 2, which contained either no support medium at all or a support medium such as mannitol, albumin or one or more powdered fibrin adhesive components, and then spray-dried in the fluidized bed. The process was performed under the following conditions:

| | |
|---|---|
| Input temperature: | 30° Celsius |
| Output temperature: | 25° Celsius |
| Spraying pressure: | 2.5 bar |
| Spraying rate: | 3.0 to 8.0 g/min |

The fibrin adhesive granulate prepared in this manner had a mean particle size of approximately 100 μm; it was flowable, did not give off dust, and immediately formed a stable, cross-linked fibrin coagulum after coming into contact with an aqueous solution.

EXAMPLE 6

Preparation of a Biodegradable Bandage Coated with Fibrin Adhesive 250 mg fibrin adhesive powder or granulate was placed on a 50×50 $mm^2$ Type 6 Ethisorb® patch (Ethicon GmbH) and distributed evenly (=10 mg fibrin adhesive powder or granulate per $cm^2$). Then a total of 2.5 ml of a solution of isopropanol/20% PEG 6000 was sprayed evenly on the coating. The biodegradable bandage obtained after the evaporation of the isopropanol was comprised of a support medium and fibrin adhesive coating with good adhesion and did not crumble after bending.

EXAMPLE 7

Preparation of a Biodegradable Bandage Coated with Fibrin Adhesive 60 mg fibrin adhesive powder or granulate was applied to a 20×30 mm² Type 6 Vicryl-fleece (Ethicon GmbH) and spread evenly (=10 mg powder per cm²). Then a total of 0.6 ml of a solution of isopropanol/20% PEG 6000 was sprayed evenly on the coating. After the isopropanol had evaporated, a flexible, biodegradable bandage with a fibrin adhesive coating and good adhesion was obtained.

EXAMPLE 8

Collagen Fleece Coated with Fibrin Adhesive

The Interceed collagen fleece (Johnson & Johnson), size 50×50 mm², was mixed evenly with 250 mg fibrin adhesive powder or granulate. Then a total of 0.6 ml of a solution of isopropanol/10% PEG 6000 was sprayed evenly on the coating. After the isopropanol had evaporated, a combined fibrin adhesive collagen fleece was obtained.

The invention claimed is:

1. A preparation comprising a fibrin adhesive granulate comprising granulate pellets with a particle size in the range from approximately 50 μm to approximately 1000 μm, wherein the granulate pellets comprise thrombin, Factor XIII, fibrinogen, and a calcium salt; and
   wherein the preparation comprises one or more of a wound care fleece, a bandage, a plaster, and a hydrophilic non-aqueous salve base, or wherein the preparation is an effervescent preparation.

2. The preparation according to claim 1, wherein the preparation is an effervescent preparation further comprising one or more substances required for the formation of $CO_2$.

3. The effervescent preparation according to claim 2, wherein the granulate pellets have a particle size in the range from approximately 100 μm to approximately 200 μm.

4. The effervescent preparation according to claim 2, wherein the one or more substances required for the formation of $CO_2$ comprise a mixture of a carbonate and a physiologically safe organic acid.

5. The effervescent preparation according to claim 2, further comprising one or more substances that promote wound healing.

6. The effervescent preparation according to claim 5, wherein the one or more substances that promote wound healing are chosen from immunoglobulins, chemotherapeutics, and antibiotics.

7. A tablet comprising an effervescent preparation according to claim 2.

8. The preparation according to claim 1, wherein the preparation is a wound care fleece comprising a biodegradable support medium, wherein the biodegradable support medium comprises the fibrin adhesive granulate.

9. The wound care fleece according to claim 8, wherein the wound care fleece comprises a hydrophilic, non-aqueous salve base, and wherein the salve base comprises the fibrin adhesive granulate.

10. The wound care fleece according to claim 8, wherein the biodegradable support medium comprises one or more substances chosen from natural and chemically modified collagen, keratin, gelatin, carbohydrates, and cellulose derivatives.

11. The wound care fleece according to claim 8, wherein the biodegradable support medium comprises one or more polymers chosen from polyhydroxy carboxylic acids, polyesters, polycyano acrylates, polyamino acids, polyalcohols, and silicones.

12. The wound care fleece according to claim 8, wherein the wound care fleece comprises fibrinogen in the range from approximately 0.05 mg/cm² to approximately 50 mg/cm² and thrombin in the range from approximately 1 μg/cm² to approximately 10 mg/cm².

13. The wound care fleece according to claim 8, wherein one or both sides of the fleece's support medium contain a composition comprising the fibrin adhesive granulate.

14. The preparation according to claim 1, wherein the preparation is a bandage comprising a wound care fleece comprising a biodegradable support medium, wherein the biodegradable support medium comprises the fibrin adhesive granulate.

15. The preparation according to claim 1, wherein the preparation is a plaster comprising a water proof or water permeable material.

16. The preparation according to claim 15, wherein the plaster comprises adhesive strips.

17. The preparation according to claim 1, wherein the preparation is a hydrophilic, non-aqueous salve base comprising the fibrin adhesive granulate.

18. The preparation according to claim 17, wherein the salve base comprises one or more polyols.

19. The preparation according to claim 18, wherein the one or more polyols are chosen from polyethylene glycols, polypropylene glycols, and ethylene propylene copolymers.

20. The preparation according to claim 1, wherein the fibrin adhesive granulate is prepared by:
   (a) providing solutions or suspensions of the thrombin, and the fibrinogen with factor XIII;
   (b) drying the solutions in a fluidized bed apparatus; and
   (c) forming the flowable solid granules with a particle size of approximately 50-1000 μm.

21. A method for preparing a preparation according to claim 8, comprising layering the fibrin adhesive granulate on a biodegradable support medium.

22. A method for preparing a preparation as claimed in claim 17, comprising mixing the fibrin adhesive granulate with the hydrophilic, non-aqueous salve base.

23. A method for releasing a substance comprising:
   adding the substance to a fibrin adhesive granulate comprising granulate pellets with a particle size in the range from approximately 50 μm to approximately 1000 μm, wherein said granulate pellets comprise thrombin, Factor XIII, fibrinogen, and a calcium salt; and
   applying a preparation comprising the fibrin adhesive granulate to a desired site, wherein the substance is chosen from biological, vegetable and synthetic factors.

24. The method according to claim 23, wherein the substance supports wound healing or acts as an antifibrinolytic, antibiotic, chemotherapeutic or immune modulator.

* * * * *